United States Patent
Copple et al.

(10) Patent No.: US 11,058,412 B2
(45) Date of Patent: Jul. 13, 2021

(54) SUTURE DELIVERY DEVICE

(71) Applicant: Paragon Surgical LLC, Fort Collins, CO (US)

(72) Inventors: Zachary S. Copple, Fort Collins, CO (US); Asheesh Bedi, Ann Arbor, MI (US)

(73) Assignee: Paragon Surgical LLC, Fort Collins, CO (US)

( * ) Notice: Subject to any disclaimer, the term of this patent is extended or adjusted under 35 U.S.C. 154(b) by 423 days.

(21) Appl. No.: 15/562,115

(22) PCT Filed: Mar. 25, 2016

(86) PCT No.: PCT/US2016/024356
§ 371 (c)(1),
(2) Date: Sep. 27, 2017

(87) PCT Pub. No.: WO2016/160619
PCT Pub. Date: Oct. 6, 2016

(65) Prior Publication Data
US 2018/0078251 A1    Mar. 22, 2018

Related U.S. Application Data

(60) Provisional application No. 62/139,448, filed on Mar. 27, 2015.

(51) Int. Cl.
*A61B 17/04*    (2006.01)
*A61B 17/06*    (2006.01)
*A61B 17/00*    (2006.01)

(52) U.S. Cl.
CPC ...... *A61B 17/0469* (2013.01); *A61B 17/0482* (2013.01); *A61B 17/0485* (2013.01);
(Continued)

(58) Field of Classification Search
CPC ............ A61B 17/0469; A61B 17/0482; A61B 17/0485; A61B 2017/00358;
(Continued)

(56) References Cited

U.S. PATENT DOCUMENTS 5,462,560 A    10/1995  Stevens
2003/0236536 A1*  12/2003  Grigoryants ....... A61B 17/0469
                                                606/151
(Continued)

FOREIGN PATENT DOCUMENTS

WO    WO-03/077771 A1    9/2003
WO    WO-2013/192006 A1    12/2013

*Primary Examiner* — Shaun L David
*Assistant Examiner* — Christina C Lauer
(74) *Attorney, Agent, or Firm* — Mintz Levin Cohn Ferris Glovsky and Popeo, P.C.

(57) ABSTRACT

Disclosed is a suture delivery device for endoscopically passing a suture into biological tissue. The device can include two hypodermic needles that can be manipulated via controls on a handle of the device in order to pass a suture from one needle to the other. For example, the device can include a first needle coupled to at least one loop member that, when deployed from the first needle, provides a target through which a second needle of the device can deliver the suture. Once the second needle intersects the loop member, the user can advance a length of suture out through a distal end of the second needle. The loop member can then be retracted into the first needle, thereby grabbing and securing the suture in the process.

19 Claims, 8 Drawing Sheets

(52) U.S. Cl.
CPC .............. *A61B 2017/00358* (2013.01); *A61B 2017/00438* (2013.01); *A61B 2017/0472* (2013.01); *A61B 2017/061* (2013.01); *A61B 2017/0608* (2013.01); *A61B 2017/06052* (2013.01)

(58) Field of Classification Search
CPC .... A61B 2017/06052; A61B 2017/061; A61B 2017/00349
See application file for complete search history.

(56) References Cited

U.S. PATENT DOCUMENTS

| | | | |
|---|---|---|---|
| 2005/0209613 A1* | 9/2005 | Roop | A61B 17/0057 606/144 |
| 2008/0154286 A1 | 6/2008 | Abbott et al. | |
| 2010/0114123 A1* | 5/2010 | Nason | A61B 17/0469 606/147 |
| 2010/0198235 A1 | 8/2010 | Pierce et al. | |
| 2011/0295279 A1* | 12/2011 | Stone | A61B 17/0469 606/145 |
| 2014/0058417 A1 | 2/2014 | Levy et al. | |
| 2014/0207158 A1 | 7/2014 | Stone et al. | |

\* cited by examiner

SUTURE DELIVERY DEVICE

CROSS-REFERENCE TO RELATED APPLICATION

The current application is a national stage entry, filed under 35 U.S.C. § 371, of PCT/US2016/024356, filed Mar. 25, 2016, and claims priority under 35 U.S.C. § 119(c) to U.S. Provisional patent application Ser. No. 62/139,448, filed on Mar. 27, 2015, and entitled "Suture Delivery Device," which are incorporated by reference herein in their entirety.

TECHNICAL FIELD

The subject matter described herein relates to a handheld suture delivery device.

BACKGROUND

Endoscopic surgical procedures provide several advantages over invasive surgical procedures. For example, compared to endoscopic procedures, invasive surgical procedures can require larger incisions and longer surgical times. This can result in greater medical costs and healing time, as well as increased risk of complications experienced by the patient during and after surgery. Various endoscopic devices have been developed and used for assisting with, for example, cutting, grasping, and cauterizing tissue. During some endoscopic procedures, it can be difficult to effectively and efficiently stitch tissue, such as tissue that is located a distance below the surface tissue. For example, it can be difficult to view the stitching site and sufficiently perform such stitching without increasing the previously formed incision or forming a new surgical incision.

SUMMARY

Aspects of the current subject matter can include a handheld suture delivery device that can pass and receive a stitch through tissue located a distance beneath a surface tissue (e.g., skin) via a single small incision. The single small incision can be, for example, no larger than the one required to perform an endoscopic surgical procedure proceeding the passing and retrieving of the stitch. The device can also perform the passing, retrieving, and forming of the stitch without a user having to view the stitching site.

In one aspect, a suture delivery device for endoscopically delivering a suture through soft tissue is described that can include a handle sized and shaped to be grasped by a user. In addition, the suture delivery device can include a first elongated needle extending outwardly from the handle. The first elongated needle can be hollow and have a proximal, straight section attached to the handle and a distal, curved section with a sharpened distalmost tip. Additionally, the suture delivery device can include a flexible loop member slidably positioned inside the first elongated needle. The flexible loop member can be movable between a retracted position inside the first elongated needle and a deployed position outside of the distalmost tip of the first elongated needle. Furthermore, the suture delivery device can include a second elongated needle extending outwardly from the handle adjacent the first elongated needle. The second elongated needle can be hollow and movable between a first position entirely outside the loop member and a second position where a distal end of the second needle intersects the loop member when the loop member is in the deployed position. The distal end of the second elongated needle can be aligned to allow the loop member to grasp the second elongated needle when the second elongated needle is in the second position. The suture delivery device can also include a suture slidably positioned along the second elongated needle for aligning the suture within the loop member.

In another aspect, an implementation of the suture delivery device for endoscopically delivering a suture through soft tissue is described that can include a handle sized and shaped to be grasped by a user and a first elongated needle extending outwardly from the handle. The first elongated needle can be hollow with a sharpened distalmost tip. Additionally, the suture delivery device can include a flexible loop member slidably positioned inside the first elongated needle. The flexible loop member can be movable between a retracted position inside the first elongated needle and a deployed position outside of the distalmost tip of the first elongated needle. Furthermore, the suture delivery device can include a second elongated needle extending outwardly from the handle adjacent the first elongated needle. The second elongated needle can be hollow and have a proximal, straight section attached to the handle and a distal, curved section with a sharpened distalmost tip. The second elongated needle can be movable between a first position entirely outside the loop member and a second position where a distal end of the second needle intersects the loop member when the loop member is in the deployed position. The distal end of the second elongated needle can be aligned to allow the loop member to grasp the second elongated needle when the second elongated needle is in the second position. The suture delivery device can also include a suture slidably positioned along the second elongated needle for aligning the suture within the loop member.

In some variations one or more of the following features can optionally be included in any feasible combination. For example, the suture delivery device can further include at least one control member associated with the handle for controlling movement of at least one of the flexible loop member, the second elongated needle, and the suture. The suture extends at least one of parallel to and in line with a longitudinal axis of the second elongated needle, the longitudinal axis intersecting a part of the flexible loop such that advancement of the suture along the second elongated needle allows the suture to intersect the flexible loop thereby allowing the flexible loop to grasp the suture. The suture delivery device can further include a cannula extending from the handle, with the second elongated needle being movable relative to the cannula and extending along an inner passageway of the cannula. The shape of the loop member when in the deployed position can include one or more of a spherical shape, an oblong shape, a cylindrical shape, and a square shape. The loop member can include at least one flexible member extending between a proximal loop end and a distal loop end and at least one flexible member can be made out of Nitinol. The loop member can include a three-dimensional spherical net including more than two flexible members radially extending at an angel relative to each other.

In another interrelated aspect of the current subject matter, a method includes puncturing a distal end of a suture delivery device through tissue. The suture delivery device can include a first elongated needle extending from a handle, with the first elongated needle being hollow and having a proximal, straight section attached to the handle and a distal, curved section with a sharpened distalmost tip. The suture delivery device can further include a flexible loop member being movable between a retracted position inside the first elongated needle and a deployed position outside of the distalmost tip of the first elongated needle. In addition, the suture delivery device can include a second elongated needle extending from the handle and being movable between a first position outside the loop member and a second position where a distal end of the second needle intersects the loop member when the loop member is in the deployed position, and where the distal end of the second elongated needle can be aligned to allow the loop member to grasp the second elongated needle when the second elongated needle is in the second position. The suture delivery device can further include a suture slidably positioned along the second elongated needle for aligning the suture within the loop member. The method can further include deploying the flexible loop member from the first elongated needle, thereby allowing the flexible loop member to form the deployed position. The method can further include advancing the second elongated needle from the first position to the second position such that the distal end of the second needle intersects the loop member and advancing the suture to extend at least substantially through the flexible loop member. In addition, the method can include retracting the flexible loop member thereby grasping and securing the suture within the retracted flexible loop member.

In some variations of the method one or more of the following can optionally be included in any feasible combination. For example, the method can further include retracting the second elongated needle to the first position. In addition, the puncturing the distal end of the device can include puncturing the tissue with a distal end of the first elongated needle and advancing the second elongated needle into the second position can include puncturing the tissue with the second elongated needle. Additionally, the method can further include pulling the device in a proximal direction thereby looping the suture through the tissue to form a part of a stitch.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

When practical, similar reference numbers denote similar structures, features, or elements.

DETAILED DESCRIPTION

Figure 1:
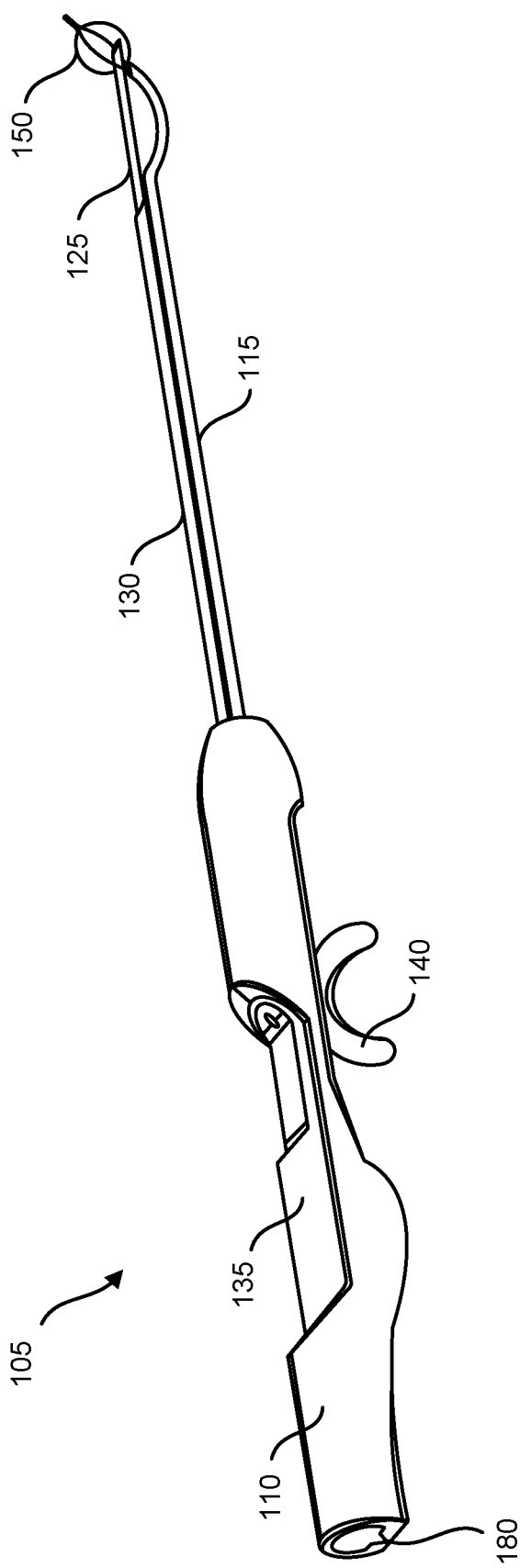
FIG. 1 shows a perspective view of an example implementation of a suture delivery device consistent with implementations of the current subject matter, which includes a first elongated needle and a second elongated needle extending from a handle configured to be held by a hand of a user.

Disclosed is a suture delivery device for endoscopically passing a suture into biological tissue. The suture delivery device can be a disposable, handheld endoscopic suture device configured to deliver and pass a suture through soft tissue and to retrieve a stitch through soft tissue through a single portal or opening in tissue. As described in detail below the device includes two hypodermic needles that can be manipulated by an operator via controls on a handle of the device in order to pass a suture from one needle to the other. For example, the device can include a first needle coupled to at least one loop member that, when deployed from the first needle, provides a target through which a second needle of the device can deliver the suture. Once the second needle intersects the loop member, the user can advance a length of suture out through a distal end of the second needle. The loop member can then be retracted into the first needle, thereby grabbing and securing the suture in the process, as described in detail below.

The disclosed device provides several advantages over existing suture delivery devices. For example, the suture delivery device allows a user to pass either a "simple" or a "mattress" stitch based on the needs of the user. This is achieved by the suture being advanced inside of an independently controlled, hollow needle of the device. Moreover, because one of the needles of the device is curved, the device allows the user to vary the size of the mattress stitch depending on how deep the user punctures tissue with the needle. The device also allows the user to pass a suture "blind." This means the user can pass suture where there is not a clear view of the distal end of the device. Furthermore, the device disclosed herein can stitch tissue via an incision corridor previously created during the proceeding steps of the surgical procedure, which can include endoscopic surgical procedures. As such, no further incisions need be created to perform stitching of tissue. This can reduce surgical procedure time, as well as recovery time.

In some implementations, the device can include one or more control mechanisms associated with the handle of the device. For example, the device can include a first control member that can be actuated with an index finger for deploying and retracting the loop member. In addition, the device can include a second control member, or 'thumb slide' control, that permits the user to independently advance and retract the second needle relative to the loop member, such as for intersecting the second needle with the loop member. The suture can also be advanced and retracted along the device, such as by an exposed suture pathway along the device that allows a user to manipulate the suture, such as pushing the suture to advance or pulling the suture to retract relative to the distal end of the device. In some implementations, the thumb slide can advance both the loop member from the first needle and the second needle, along with allowing the suture to be advanced from the second needle. As such, each action required to create a stich can include a separate control and/or action, however, in some implementations a single control can be included that performs all of the steps required by the device to create a stitch.

Some implementations of the loop member can include one or more loops or flexible members that can be retracted and deployed from either the first or second needle. In the deployed state, the loop member can have a variety of sizes and shapes for capturing at least the suture for grasping and pulling the suture to create a stitch, such as through soft tissue. In some implementations, the loop member can include multiple loops to form a three dimensional target through which the straight needle can deliver a suture. By delivering the suture inside the needle through the loop, the device prevents the stitch from getting caught on obstructions during operation of passing the stitch. In addition, by having the loop member close on the needle that delivers the suture, it can provide tactile feedback to the user, ensuring the user that the suture (contained with the needle) has been captured by the loop member. Furthermore, in the deployed state, the loop member can have any of a variety of sizes and shapes, including three dimensional shapes. For example, in the deployed state, the loop member can have a spherical shape, an oblong shape (e.g., where the larger part of the oblong shape is closer to the distal end of the first needle), a square shape, a cylindrical shape, etc. The flexible members can extend between a proximal end and a distal end of the loop member. The flexible members can be made out of one or more of a variety of materials, such as shape-memory materials and/or Nitinol.

In some implementations, either the first or second needle can include a crescent shape and made out of a stainless steel hypodermic tubing (e.g., 16 RW gauge). In some implementations, either the first or second needle can be made out of straight stainless steel hypodermic tubing (e.g., 17 TW gauge). The flexible members can be made out of one or more Nitinol wires, with each wire having a diameter of approximately 0.008 inch to approximately 0.0017 inch. The overall length of the device can be approximately five inches to approximately nine inches. However, other variations in shapes and sizes pertaining to the device and its parts have been contemplated and are within the scope of this disclosure.

FIG. 1 shows a perspective view of an example embodiment of a suture delivery device 105. The device 105 includes a handle 110 that is sized and shaped to be grasped by a single hand of the user. A first, hollow, elongated needle 115 extends outwardly from the handle 110. The first needle has an elongated, straight region and a curved region 120 located at a distalmost end of the needle 115. A second needle 125 is slidably positioned inside an elongated, straight cannula 130 that is positioned adjacent and/or abutting the first needle 115. The second needle 125 is attached at a proximal region to a control member, such as a thumb slide 135, that a user can actuate to slidably move the second needle 125 relative to the cannula 130. In an embodiment, the user actuates the control member by sliding it relative to the handle. In this manner, the user can slidably move a distal end of the second needle 125 into and out of a distal end of the cannula 130, as described in more detail below.

The distal or curved region of the first needle 115 can have a semi-circular shape or any of a variety of shapes. For example, the distal end of the first needle can be shaped such that it is directed towards a longitudinal axis of the second needle. In this configuration, the second needle can advance and retract directly over and/or in line with the distal end of the first needle 115.

The handle 110 can have any of a variety of shapes. In the illustrated embodiment, the handle 110 has an elongated, ergonomic shape that can comfortably fit within the hand of the user. A finger catch 140, such as a curved structure, is disposed on the handle 110 to permit a user to insert his or her index finger therein and suitably grasp on to the handle 110.

With reference still to FIG. 1, a flexible loop member 150 can be movably disposed inside the first needle 115 such that the loop member 150 can be deployed outwardly from a distal end of the first needle 115. The loop member 150 can be made of a deformable, malleable material. The loop member 150 can be manipulated by a user using a control on the handle, such as by using the thumb slide 135 or the finger catch 140. In this regard, the loop member 150 can be retracted into the curved region of the first needle 115. The loop member 150 can also be extended or deployed so that it protrudes out of the curved region of the first needle 115, as shown in FIG. 1. The loop member 150 can be attached or otherwise coupled at a proximal end to a control member on the handle 110 such as to the thumb slide 135 or the finger catch 140.

The user can achieve movement of the loop member 150 into and out of the distal end of the first needle 115 by slidably moving the appropriate control feature relative to the handle. For example, the user can move the finger catch 140 in a backward direction (proximal direction) to deploy and slide the loop member 150 out of the distal end of the first needle 115. Likewise, the finger catch 140 can move in a distal direction to slide or retract the loop member 150 into the distal end of the first needle 115. In an alternate embodiment, the user manipulates a control feature other than the finger catch to control movement and positioning of the loop member 150. For example, the user can manipulate the thumb slide 135 to control movement and positioning of the loop member 150 in an alternate embodiment.

In addition, a suture (S) is slidably positioned inside an internal lumen of the second needle 125. The suture is configured to be positioned through tissue (T) and formed into a knot or stitch using the device 105. As described in more detail below, a user can manipulate the device 105 to extend or retract the suture relative to the distal end of the second needle 125.

Figure 2:
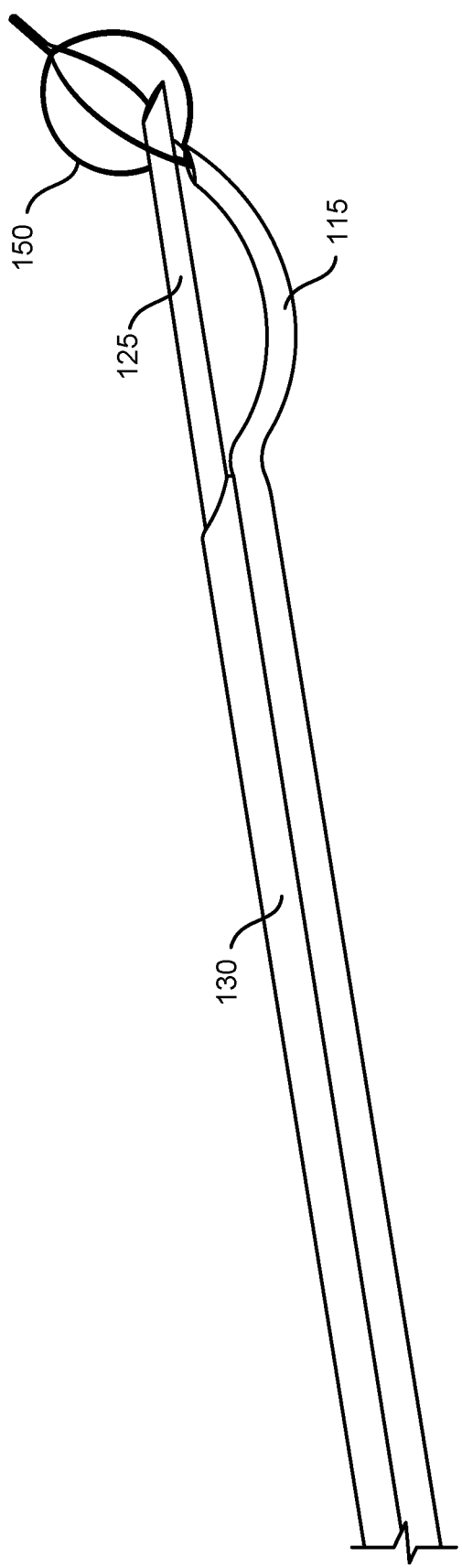
FIG. 2 shows a partial view of the suture delivery device of FIG. 1 illustrating a distal end of the device, including showing the second needle in an advanced or second position such that a distal end of the second needle intersects a loop member deployed from a distal end of the first needle.

FIG. 2 shows an enlarged view of a distal most region of the device 105 including the first needle 115 and second needle 125 extending from the cannula 130. The second needle 125 has an orientation that aims the distal tip of the second needle 130 toward the distal tip of the first needle 115. That is, the second needle 125 is aligned with an axis that extends toward the distal tip of the first needle 115. In this manner, the second needle 125 can be positioned such that its distal tip extends adjacent the distal tip of the first needle and intersects the loop member 150, as shown in FIG. 2. As mentioned, the second needle 125 is slidably positioned inside the cannula 130 such that the second needle 125 can be moved between the position shown in FIG. 2, and a position in which the distal end of the second needle 125 is located inside the cannula 130 or not intersecting the loop member 150. The user can slide the thumb slide 135 in a proximal or distal (FIG. 1) direction to achieve a corresponding movement of the second needle 125.

In some implementations, any of the control members, such as the thumb slide 135, can include one or more detents that control the positioning of the associated control member. For example, the thumb slide 135 can include a detent that locks the thumb slide 135 in the distal direction to hold the distal end of the second needle such that it is intersecting the loop member 150. The detents can be secure enough to hold the placement of the control member, yet allow the user to move the control member in and out of position.

As shown in FIG. 2, the loop member 150 is formed of a plurality of strands that collectively form a three-dimensional looped shape. That is, the strands are formed in a plurality of arcs or appropriate shapes that collectively define a sphere or globe through which the second needle 125 can be slidably positioned. Note that the distal end of the second needle 125 can be moved so that it is positioned inside and/or intersects the globe defined by the strands of the loop member 150. As mentioned, the second needle 125 is movable via a control feature on the handle so that the second needle 125 can be retracted into the cannula or sheath member 130. A suture can be advanced along the second needle 125 and extend a distance from the distal end of the second needle 125. The second needle can be retracted such that it no longer intersects the loop member 150 while allowing the suture to intersect and/or extend through the loop member 150. The loop member 150 can collapse or retract thereby grasping and securing the suture within the collapsed loop member 150. This can allow the loop member 150 to pull on the suture, such as through tissue and assist with stitching the tissue with the suture.

With reference to FIGS. 3A-3H, the operation of the suture delivery device is now described in further detail with regard to another implementation of the suture delivery device 205. The device 205 includes a similar or same features compared to device 105, such as a first needle 215, second needle 225, cannula 230, loop member 250, handle 210, first control member or thumb slide 235, and second control member or finger catch 240, as described above. However, the suture delivery device 205 includes a pyramidal shaped second control member 240 that can provide improved ergonomics. Similar to as described above, the user can grasp the handle 210 of the device 205 with a single-hand. The handle 210 has an ergonomic design so that the user can easily position his or her thumb on the thumb slide 235 and finger (e.g., index finger) on the second control member 240.

Figure 3A:
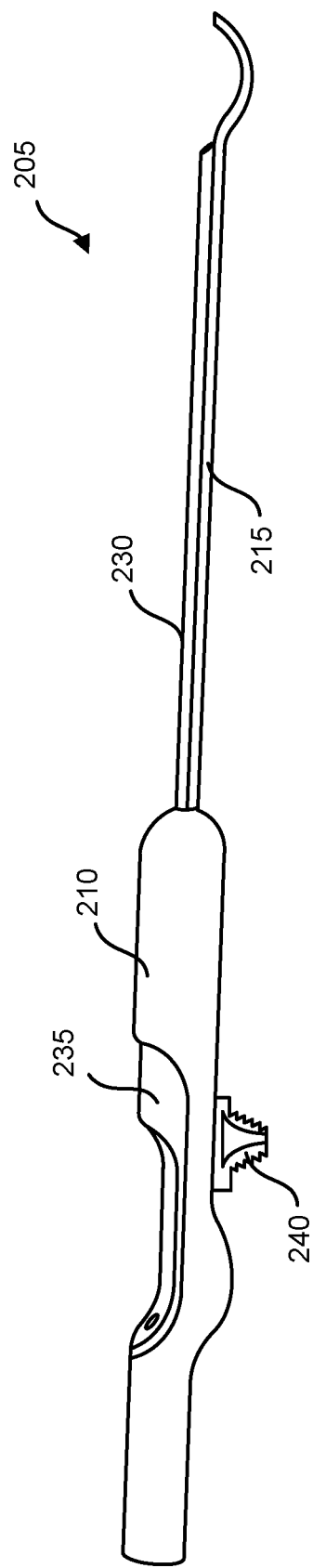
FIG. 3A shows a side perspective view of another implementation of the suture delivery device consistent with implementations of the current subject matter and showing the suture delivery device where a first and second control are in non-activated positions such that the second needle is in a first position and the loop member is retracted position.

As shown in FIG. 3A, in a default state of the device 205, the loop member 250 can be retracted into the first needle 215 so that the loop member 250 is initially not visible. In addition, the second needle 225 can be retracted inside the sheath 230 and the suture can be positioned entirely inside the second needle 225, which is also contained inside the sheath 230 and not visible, as shown in FIG. 3A. In addition, FIG. 3A shows an example of the first control member or thumb slide 235 in an example non-activated position, thereby placing the second needle 230 in a first position where it is retracted inside the sheath 230. The second control member or finger catch 240 is also shown in a non-activated position, thereby placing the loop member 250 in the non-visible retracted position inside the first needle 215.

Figure 3B:
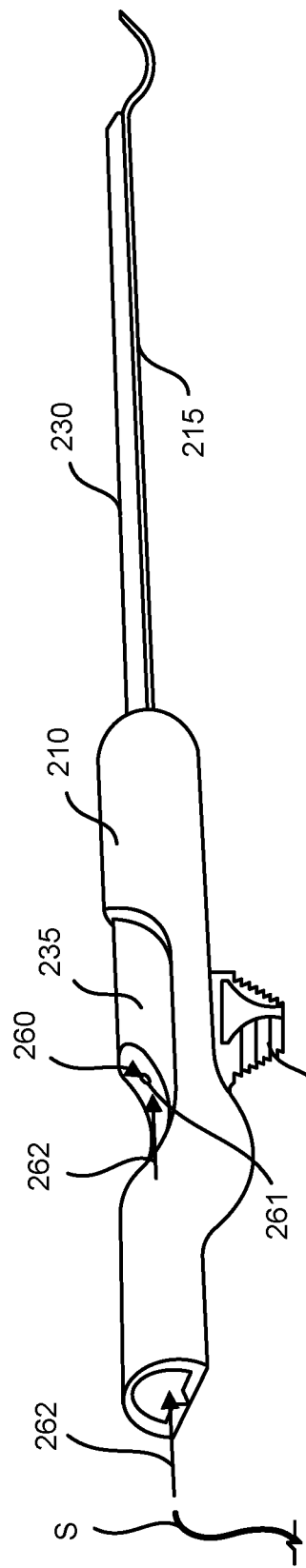
FIG. 3B shows a side perspective view of the suture delivery device of FIG. 3A showing a part of a suture pathway for inserting and extending suture along the device.
Figure 3C:
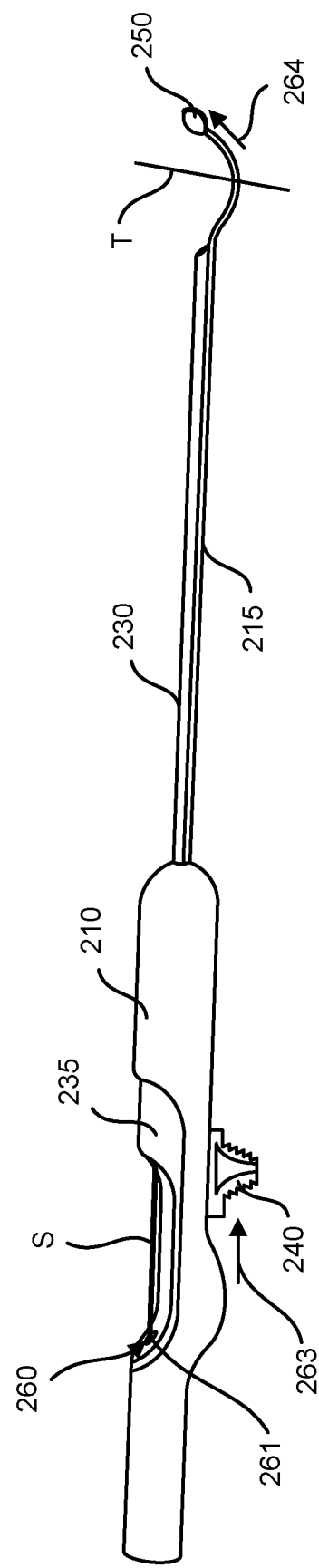
FIG. 3C shows a side perspective view of the suture delivery device of FIG. 3A showing advancing the first control thereby deploying the loop member from the distal end of the first needle.

As shown in FIG. 3B, the device can include a suture pathway 260 that extends along at least a part of the device 205 and is sized to allow the suture to slidably travel along the suture pathway 260. The suture pathway 260 can extend at least along the second needle 230 and along a length of the first control member 235. In some implementations, the suture pathway 260 can extend through the handle 210 and between pathway outlets 261 along the first control member 235, as shown in FIGS. 3B and 3C. As such, suture (S) can be advanced along the suture pathway 260 (including along arrows 262 in FIG. 3B) such that the suture extends between the pathway outlets 261, thereby exposing a length of the suture along a part of the first control member 240. A user can manipulate the length of exposed suture extending along the first control member 235, such as moving the suture in the distal direction to extend the suture from the distal end of the second needle 230 and/or extend the suture at least substantially through the loop member when in the deployed position. In addition, the suture can be moved in the proximal direction to retract the suture, for example, from the distal end of the second needle 230.

As shown in FIG. 3C, the user can manipulate the device 205 so that the distal end of the first needle 215 is inserted through the tissue (T) to be sutured. In other words, the user inserts the distal end of the first needle 215 through tissue to be sutured, as shown in FIG. 3C, which shows a distal region of the device with the curved region of the distal needle 215 inserted through tissue (T). The user can also manipulate the second control member or finger catch 240 on the handle 210 (such as in distal direction, as shown by arrow 263) to deploy the loop member 250 (such as in angled distal direction relative to a longitudinal axis of the second needle 230, as shown by arrow 264) so that it extends out of the distal end of the first needle 215, such as is shown in FIG. 3C. As shown in FIG. 3C, the loop member 250 can extend at an angle relative to a longitudinal axis of the second needle 225 (e.g., approximately 10 degrees to approximately 90 degrees, such as 45 degrees).

Figure 3D:
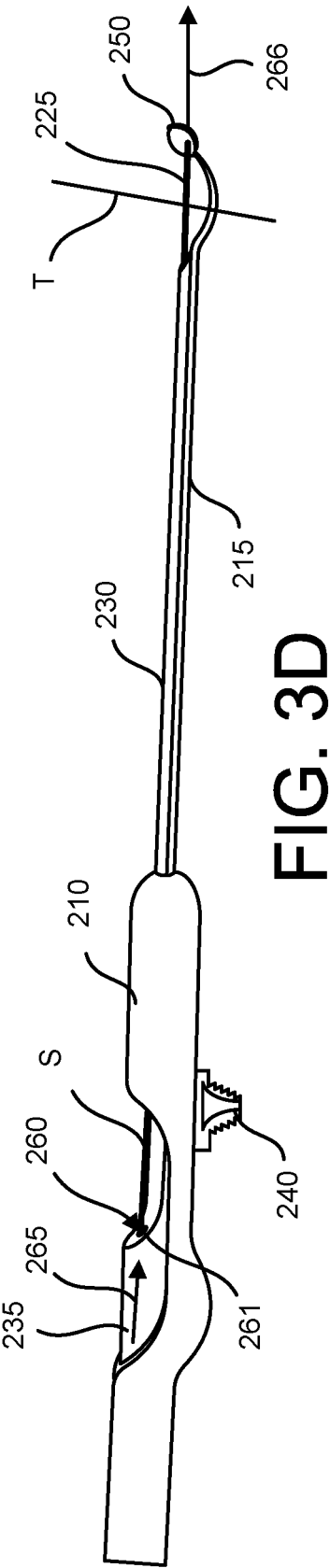
FIG. 3D shows a perspective view of the suture delivery device of FIG. 3A showing advancing the second control thereby advancing the second needle such that the distal end of the second needle intersects the loop member.
Figure 3E:
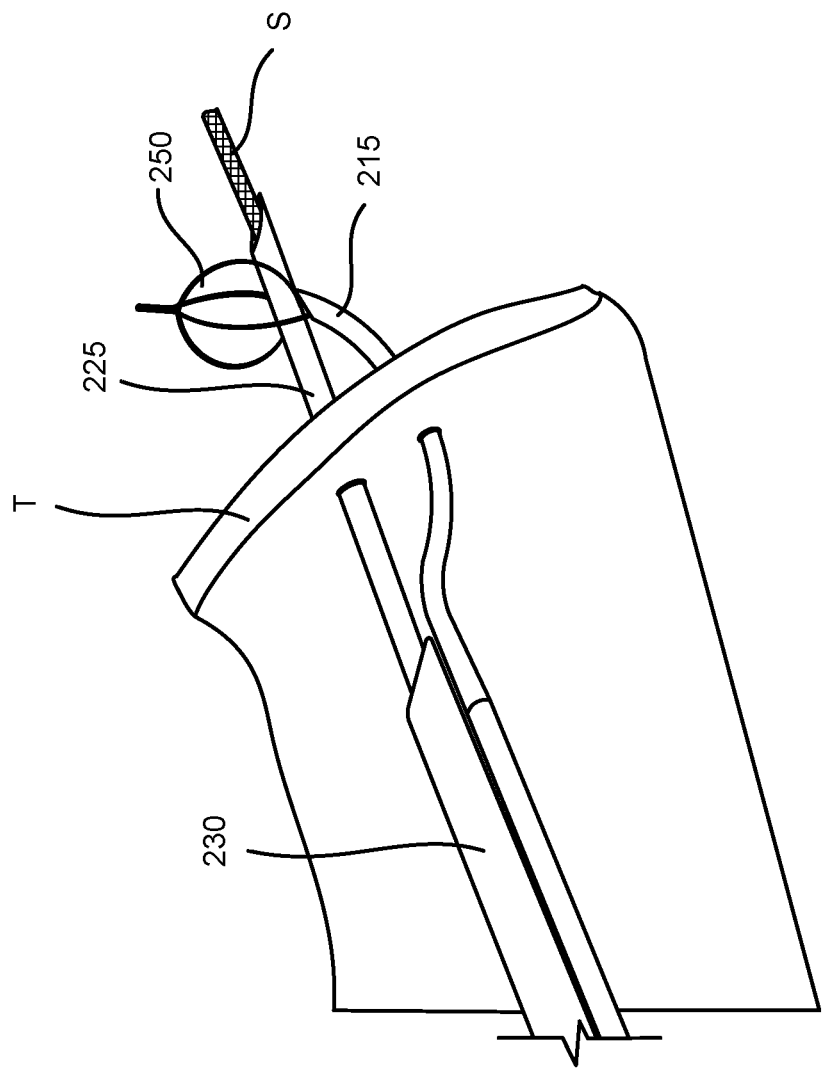
FIG. 3E shows a partial view of the suture delivery device of FIG. 3A showing the distal end of the suture delivery device with the distal end of the second needle extended through the loop member with a length of suture extending out from the distal end of the second needle.

As shown in FIG. 3D, the thumb slide 235 can be manipulated, such as by moving the thumb slide 235 in a distal direction (such as along arrow 265). In an embodiment, the thumb slide 235 moves in a direction parallel to the axes of the cannula 230. The user can extend the second needle 225 out of the sheath 230 (such as in distal direction, as shown by arrow 266) by sliding the thumb slide 235 in the distal direction relative to the handle 210. Furthermore, the user can actuate the thumb slide 235 so that the second needle 225 is in the second position where it penetrates tissue and is positioned with its distal end aimed at, located inside, and/or extending through the loop member 250, as shown in FIGS. 3D and 3E.

The length of suture (S) exposed along the second control member 235 can be advanced in the distal direction, thereby advancing suture out from the distal end of the second needle 225. The suture (S) can be extended out from the distal end of the second needle 225 when the distal end of the second needle is extending through at least a part of the loop member 250. In this state, the curved region of the first needle 215 has penetrated the tissue to be sutured, the distal end of the second needle 225 has also penetrated the tissue to be sutured, the loop member 250 is deployed from the first needle 215, the distal end of the second needle 225 intersects the loop member 250, and a length of suture extends from the distal end of the second needle 225, as shown in FIG. 3E.

Figure 3F:
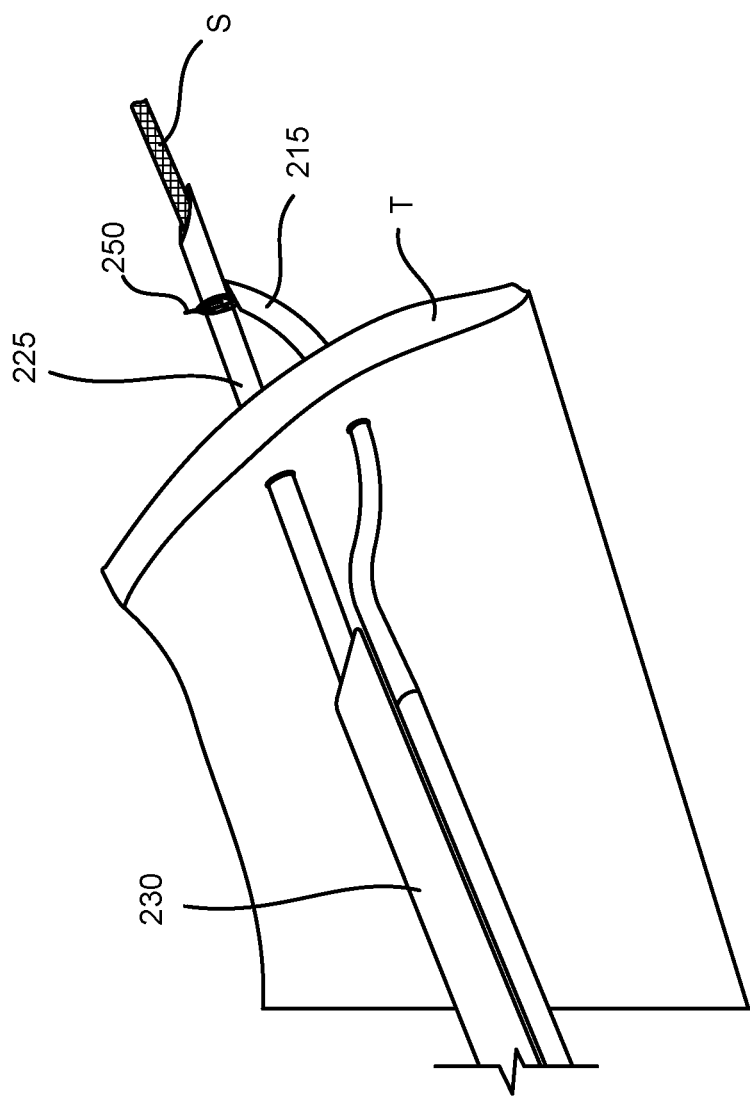
FIG. 3F shows a partial view of the suture delivery device of FIG. 3A showing the distal end of the suture delivery device with the loop member collapsed around an outer surface of the second needle.
Figure 3G:
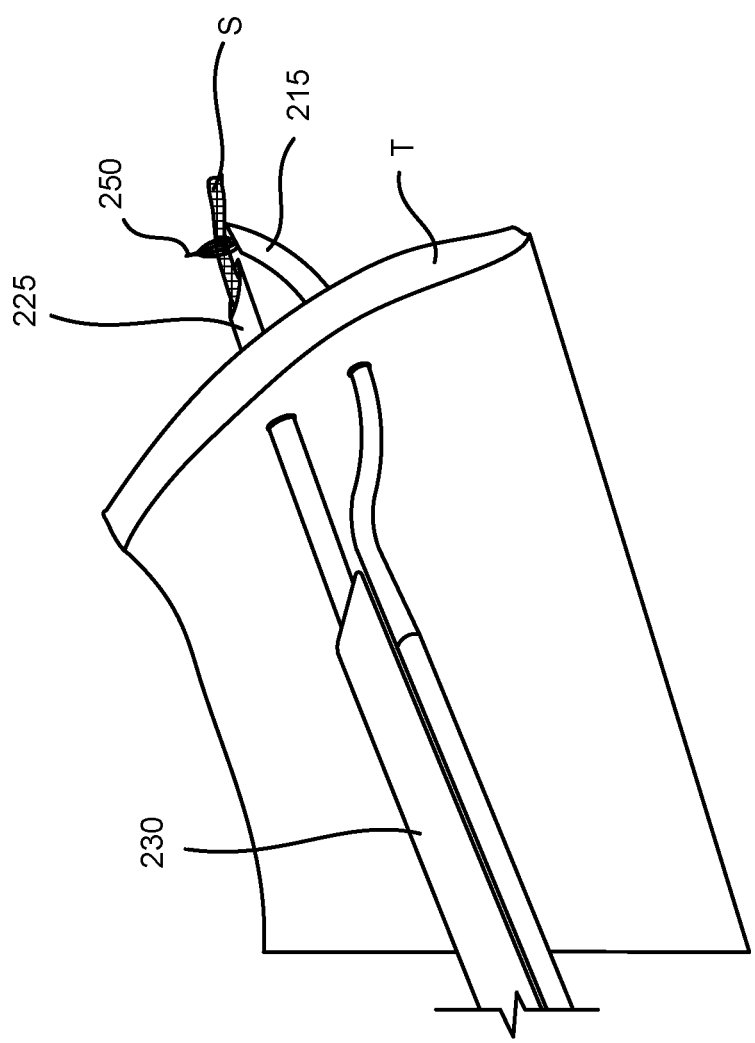
FIG. 3G shows a partial view of the suture delivery device of FIG. 3A showing the distal end of the suture delivery device with the loop member collapsed around the suture extending from the second needle.

With a length of suture (S) extending from the second needle 225 and/or at least substantially through the loop member 250, the loop member 250 can be retracted into the first needle 215 using the appropriate control on the handle 210 (e.g., moving the finger catch 240 in the proximal direction). As the loop member 250 retracts, it can collapse and grasp the suture (S) and/or the second needle 225 (as shown in FIG. 3F). If the retracting loop member 250 grasps the second needle 225 while the second needle 225 is in the second position, as shown in FIG. 3F, the second needle 225 can be slidably disengaged from the loop member 250 using an appropriate control on the handle 210 (e.g., moving the thumb slide 235 in the proximal direction to move the second needle 225 to the first position). Movement of the second needle 225 can be independent of the suture such that when the second needle 225 is retracted and no longer intersects the loop member 250, the suture can then be grasped and secured by the loop member 250, as shown in FIG. 3G.

Figure 3H:
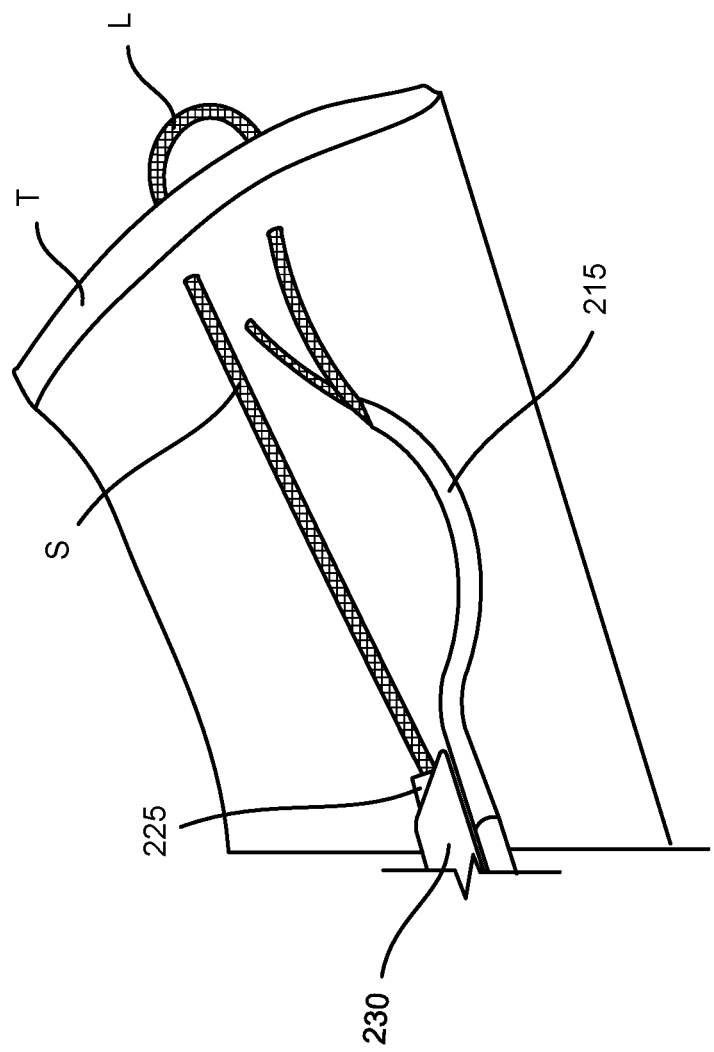
FIG. 3H shows a partial view of the suture delivery device of FIG. 3A showing a suture stitch through tissue formed by the suture delivery device with the suture extending between the second needle and the first needle.

As shown in FIG. 3H, the loop member 250 can pull the suture toward or into the distal end of the first needle 215. At this point, suture is extending between distal ends of the first needle 215 and the second needle 225. The second needle 225 can also be retracted back into the sheath 230 and both the second needle 225 and the first needle 215 can retract or get pulled back such that they no longer penetrate the tissue (T). With the loop member 250 grasping the suture (S) and the suture extending through the second needle 225, the entire device can be pulled back in a proximal direction thereby forming a loop (L) of suture through tissue, as shown in FIG. 3H. For example, a knot can then be formed after release of the loop member 250 on the suture. However, the suture is not limited to being tied in a knot and can, alternatively or in addition, be secured to any number of features or structures, such as, for example, an implant (e.g., bone implant, spinal implant, etc.) without departing from the scope of this disclosure. For example, the above steps can be repeated to form any number of suture loops and stitches along the tissue or associated features (e.g., mesh implant, etc.).

In some implementations, the handle can include a suture lock 280 (see also suture lock 180 in FIG. 1) that can releasably prevent the advancing or retracting of suture (S) relative to the handle 210. The suture lock 280, for example, can include a notch or crevice that allows the suture to wedge or secure therewithin. However, any number of features for preventing the advancing or retracting of suture relative to the handle is within the scope of this disclosure.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flow(s) when depicted in the accompanying figures and/or described herein do not necessarily require the particular order shown, or sequential order, to achieve desirable results. Other implementations may be within the scope of the following claims.

The invention claimed is:

1. A suture delivery device for endoscopically delivering a suture through soft tissue, comprising:
 a handle sized and shaped to be grasped by a user;
 a first elongated needle extending outwardly from the handle, the first elongated needle being hollow and having a proximal, straight section attached to the handle and a distal, curved section with a sharpened distalmost tip;
 a flexible loop member slidably positioned inside the first elongated needle, the flexible loop member being movable along the first elongated needle, the flexible loop member forming a deployed configuration outside of the distalmost tip of the first elongated needle when the flexible loop member is in a deployed position;
 a second elongated needle extending outwardly from the handle adjacent the first elongated needle, the second elongated needle being hollow and movable between a first position entirely outside the flexible loop member and a second position where a distal end of the second needle intersects the flexible loop member when the flexible loop member is in the deployed position to thereby allow the flexible loop member to grasp the second elongated needle when the second elongated needle is in the second position; and
 a suture slidably positioned along the second elongated needle for aligning the suture within the flexible loop member,
 wherein the flexible loop member forms a first retracted configuration and a second retracted configuration, the first retracted configuration including the flexible loop member conforming around a part of the second elongated needle when the second elongated needle is in the second position and the flexible loop member is in the first retracted position, the second retracted configuration including the flexible loop member conforming around a part of the suture when the second elongated needle is in the first position and the flexible loop member is in the second retracted position.

2. The suture delivery device of claim 1, further comprising at least one control member associated with the handle for controlling movement of at least one of the flexible loop member, the second elongated needle, and the suture.

3. The suture delivery device of claim 1, wherein the suture extends at least one of parallel to and in line with a longitudinal axis of the second elongated needle, the longitudinal axis intersecting a part of the flexible loop in the deployed configuration such that advancement of the suture along the second elongated needle allows the suture to intersect the flexible loop thereby allowing the flexible loop to grasp the suture.

4. The suture delivery device of claim 1, further comprising a cannula extending from the handle, the second elongated needle being movable relative to the cannula and extending along an inner passageway of the cannula.

5. The suture delivery device of claim 1, wherein the flexible loop member in the deployed configuration includes one or more of a spherical shape, an oblong shape, a cylindrical shape, and a square shape.

6. The suture delivery device of claim 1, wherein the flexible loop member comprises at least one flexible member extending between a proximal loop end and a distal loop end.

7. The suture delivery device of claim 6, wherein the at least one flexible member is made out of Nitinol.

8. The suture delivery device of claim 1, wherein the flexible loop member comprises more than two flexible members that collectively form a three-dimensional spherical shape when the flexible loop member is in the deployed position.

9. The suture delivery device of claim 1, wherein the flexible loop member, when in the deployed position, forms a three dimensional shape configured to allow the second elongated needle to intersect the flexible loop member when the second elongated needle is in the second position.

10. A suture delivery device for endoscopically delivering a suture through soft tissue, comprising:
a handle sized and shaped to be grasped by a user;
a first elongated needle extending outwardly from the handle, the first elongated needle being hollow with a sharpened distalmost tip;
a flexible loop member slidably positioned inside the first elongated needle, the flexible loop member being movable along the first elongated needle, the flexible loop member forming a deployed configuration outside of the distalmost tip of the first elongated needle when the flexible loop member is in a deployed position;
a second elongated needle extending outwardly from the handle adjacent the first elongated needle, the second elongated needle being hollow and having a proximal, straight section attached to the handle and a distal, curved section with a sharpened distalmost tip, the second elongated needle being movable between a first position entirely outside the flexible loop member and a second position where a distal end of the second needle intersects the flexible loop member when the flexible loop member is in the deployed position to thereby allow the flexible loop member to grasp the second elongated needle when the second elongated needle is in the second position; and
a suture slidably positioned along the second elongated needle for aligning the suture within the flexible loop member,
wherein the flexible loop member forms a first retracted configuration and a second retracted configuration, the first retracted configuration including the flexible loop member conforming around a part of the second elongated needle when the second elongated needle is in the second position and the flexible loop member is in the first retracted position, the second retracted configuration including the flexible loop member conforming around a part of the suture when the second elongated needle is in the first position and the flexible loop member is in the second retracted position.

11. The suture delivery device of claim 10, further comprising at least one control member associated with the handle for controlling movement of at least one of the flexible loop member, the second elongated needle, and the suture.

12. The suture delivery device of claim 10, wherein the flexible loop member in the deployed configuration includes one or more of a spherical shape, an oblong shape, a cylindrical shape, and a square shape.

13. The suture delivery device of claim 10, wherein the flexible loop member comprises at least one flexible member extending between a proximal loop end and a distal loop end.

14. The suture delivery device of claim 13, wherein the at least one flexible member is made out of Nitinol.

15. The suture delivery device of claim 10, wherein the flexible loop member comprises more than two flexible members that collectively form a three-dimensional spherical shape when the flexible loop member is in the deployed position.

16. A method comprising:
puncturing a distal end of a suture delivery device through tissue, the suture delivery device comprising:
a first elongated needle extending from a handle, the first elongated needle being hollow and having a proximal, straight section attached to the handle and a distal, curved section with a sharpened distalmost tip;
a flexible loop member being movable along the first elongated needle, the flexible loop member forming a deployed configuration outside of the distalmost tip of the first elongated needle when the flexible loop member is in the deployed position;
a second elongated needle extending from the handle and being movable between a first position outside the flexible loop member and a second position where a distal end of the second needle intersects the flexible loop member when the flexible loop member is in the deployed position to thereby allow the flexible loop member to grasp the second elongated needle when the second elongated needle is in the second position;
a suture slidably positioned along the second elongated needle for aligning the suture within the flexible loop member; and
forming, when the flexible loop member is in the deployed position, the flexible loop member into the deployed configuration;
advancing the second elongated needle from the first position to the second position such that the distal end of the second elongated needle intersects the flexible loop member;
forming, when the second elongated needle is in the second position and the flexible loop member is in a first retracted position, the flexible loop member into a first retracted configuration including the flexible loop member conforming around a part of the second elongated needle;
advancing the suture to extend at least substantially through the flexible loop member; and retracting the second elongated needle to the first position; and forming, when the second elongated needle is in the first position and the flexible loop member is in a second retracted position, the flexible loop member into a second retracted configuration including the flexible loop member conforming around a part of the suture.

17. The method of claim 16, wherein puncturing the distal end of the device through tissue comprises puncturing the tissue with a distal end of the first elongated needle.

18. The method of claim 16, wherein advancing the second elongated needle into the second position comprises puncturing the tissue with the second elongated needle.

19. The method of claim 16, further comprising:
pulling the device in a proximal direction thereby looping the suture through the tissue to form a part of a stitch.

* * * * *